(12) United States Patent
Cabre et al.

(10) Patent No.: US 11,845,944 B2
(45) Date of Patent: Dec. 19, 2023

(54) FUNGAL RUST-INDUCIBLE PROMOTER

(71) Applicants: Centre National de la Recherche Scientifique, Paris (FR); Institut National des Sciences Appliquees de Lyon, Villeurbanne (FR); Universite Claude Bernard Lyon 1, Villeurbanne (FR); BASF Agricultural Solutions Seed US LLC, Florham Park, NJ (US)

(72) Inventors: Lisa Cabre, Lyons (FR); Sophie Ducerf, Lyons (FR); Stephane Peyrard, Lyons (FR); Catherine Sirven, Lyons (FR); Bernard Pelissier, Lyons (FR)

(73) Assignees: Centre National De La Recherche Scientifique, Paris (FR); Institut National des Sciences Appliquees de Lyon, Villeurbanne (FR); Universite Claude Bernard Lyon 1, Villeurbanne (FR); BASF Agricultural Solutions Seed US LLC, Florham Park, NJ (US)

( * ) Notice: Subject to any disclaimer, the term of this patent is extended or adjusted under 35 U.S.C. 154(b) by 0 days.

(21) Appl. No.: 16/615,743

(22) PCT Filed: May 11, 2018

(86) PCT No.: PCT/US2018/032230
§ 371 (c)(1),
(2) Date: Nov. 21, 2019

(87) PCT Pub. No.: WO2018/217474
PCT Pub. Date: Nov. 29, 2018

(65) Prior Publication Data
US 2020/0102569 A1    Apr. 2, 2020

(30) Foreign Application Priority Data

May 24, 2017   (EP) .................................. 17172886

(51) Int. Cl.
*C12N 15/82* (2006.01)
(52) U.S. Cl.
CPC ..... *C12N 15/8239* (2013.01); *C12N 15/8218* (2013.01); *C12N 15/8225* (2013.01); *C12N 15/8282* (2013.01)
(58) Field of Classification Search
CPC .................................................. C12N 15/8239
USPC ........................................................ 800/278
See application file for complete search history.

(56) References Cited

U.S. PATENT DOCUMENTS

2014/0137283 A1*   5/2014   Schultheiss ............. A23L 11/00
                                                                    800/265

OTHER PUBLICATIONS

GenBank Accession AC235172. Glycine max strain Williams 82 clone GM_WBb0002N17, complete sequence. Published Mar. 12, 2009. pp. 1-39.*
Oommenn et al The Plant Cell 6:1789-1803 (Year: 1994).*
Kim et al. Plant Molecular Biology 24: 105-117 (Year: 1994).*
Grimwood Genbank Accession No. AC235172 (Year: 2009).*

* cited by examiner

*Primary Examiner* — Li Zheng (57) ABSTRACT

The disclosure relates to a promoter induced by fungal rust. More specifically, the promoter is induced by the pathogen *Phakopsora pachyrhizi*, i.e. the Asian Soybean Rust. The disclosure further provides for recombinant genes comprising the promoter and methods of producing a transgenic plant that involves introducing or providing the recombinant gene to plant cells to create transgenic plant cells, and regenerating transgenic plants from the transgenic cells.

12 Claims, 3 Drawing Sheets

Specification includes a Sequence Listing.

SEQUENCE LISTING

<160> NUMBER OF SEQ ID NOS: 7

<210> SEQ ID NO 1
<211> LENGTH: 3454
<212> TYPE: DNA
<213> ORGANISM: Glycine max

<400> SEQUENCE: 1

| | | | | | |
|---|---|---|---|---|---|
| ggcaagttgt | gaaagaacca | actccaaaat | gttatggaat | tggacttgga | agccatcatc | 60 |
| atgttattgt | tcatcttcgt | gtcgtgtctc | tctcccacag | tcctttactg | aactgatgac | 120 |
| ttatcccta | ctcttttttga | ggttttgcgt | ttgccgcaac | aaagcggggt | ccatgatcca | 180 |
| attccaattt | ccaaactacc | actattttca | gggacagcta | tctattttc | tctaatgtgg | 240 |
| ctttagtatc | attttaatat | tatgaaaatt | atttaaaatg | ataatctcaa | tcaataatat | 300 |
| gattaacttc | atgcaagact | tacactaatt | gtataaatat | ttccctcaac | atcatcgtcc | 360 |
| aatcaacttt | tcttgagaac | gggaaattga | aaattcatgg | gtcaagatgt | tgactttgt | 420 |
| atgatcttga | aaattgaaaa | cagaaacaat | tactgaggat | caggatgaac | atatacatag | 480 |
| tcattttgac | tggtatctgg | cactgacttc | tcaatatttg | actttcctg | ccaccaaaac | 540 |
| atcaatggcg | tataaaaatt | atgaagaaaa | aaaatctata | aatcaaacat | tctccaagtc | 600 |
| tatcaactaa | atataaagtt | aaaaatccaa | ttagcgttta | actgcccata | atttcggtcc | 660 |
| tttgataagg | attagcattt | aattgcccag | tgccatgact | cgtggcattt | ctttcccaat | 720 |
| agttcgaact | atatttaaca | cctcggaatc | cagtagcatt | ttctggagac | gaaaattcac | 780 |
| tactactctt | tcccatttat | ccattaaaat | caccaaaaag | ttaccgactt | tacagccatt | 840 |
| agtagctaac | tatctggaat | ttcttcagct | gtgtacgtct | ttgtcaaatg | ttaaataacc | 900 |
| ttatggtata | aaaattattt | aaattttaaa | atatttttg | tggatgaata | agagagagta | 960 |
| atttaagac | ttgattatta | atttagttgt | taaattattt | aaaatatatt | aattttagtt | 1020 |
| ctcaaatttt | aaatcactcc | tatcaggttc | tttaatcgtt | aaaaatgtct | caattaagtc | 1080 |
| ttttctgttg | gaggaccttc | cttcatcctt | tgctggcaca | gctccaaact | tatccgaatt | 1140 |
| ggagctctgg | gaaataatag | cctgtgagat | gctcgtcatt | ataatgaggg | gtgtaaatga | 1200 |
| atctctcatt | ttttaaaagt | tacatataaa | taatatattg | aatatgtaaa | atttgccctc | 1260 |
| ccctaatttc | gtgcatttga | ccatgttcat | aagttttac | acctttcata | atattaatta | 1320 |
| ttaatttat | ttttaaaaa | taagttgctc | tcctgactta | ggatctagtc | ggagtttagg | 1380 |
| gtcattttttg | cttcttgtct | atcataatct | cgaggggtgc | tccgatcatc | atcgttgtcc | 1440 |
| aattgaaatt | ggatttggaa | aattataatt | tttaacagct | tttagccgct | agaatataag | 1500 |
| accttcata | caagttaact | aagtaatttc | cggcaattat | taactaccaa | aaaagtaat | 1560 |
| aaaataaaat | aataaaaata | aaaataatgt | catatcatta | tttaaggacc | aaaatagacg | 1620 |
| agaagaacaa | aaacattcaa | caagaaaaaa | gttcaaacat | attgatcaat | tgtcaaaaaa | 1680 |
| tttaaagatc | aaaatcaaat | attaaactaa | aaacataatt | tatcatctttt | tgtaattta | 1740 |
| tttcatgtta | acttaatttc | ttttggtcca | ttgcttaggg | tttaagttta | actttaattt | 1800 |
| cgtcactaag | ttgctgccta | tccaactagc | atgtccttgc | tttgttttta | tctaattatt | 1860 |
| ttagacatta | atattcacca | taaaatttat | ccttgattaa | atcttagacc | tggcctttat | 1920 |
| ctttttcaat | gtcgttaatc | atatttctca | agcagctata | ttcatgttaa | tcattaatta | 1980 |
| aaacgccctc | taaccaaca | aagttagaag | atgaagcaga | gttggagaaa | atggtgataa | 2040 |
| aaaaatagta | ctagtattta | gaggattaaa | tagaacacaa | aagtagaaat | ccaaactaaa | 2100 |

```
tttcaaatca aatttagagg acaaaaatta caaattggta aataagtact aaaactataa    2160
agttacttta ttgataatga aaagtaagtt caattgtaaa aatataaata ttgaaaactt    2220
cccatcttaa aaccataaac tacattccat cctagcaaga agtagttggt taatcgaata    2280
gtatcgaact aaattttctt aataagattt aagatttaag ttttgtgaat gaaaaaaata    2340
taattagatg agaagaattt tactagatga ttagctagat tttctgacag aaattaatga    2400
tcggcaaaat caataaatat ttcatactaa taacacggtt taaaaaaaaa actacatccc    2460
gctcttgaat taatccttaa tgcatctttc attatattta aattgctttt tatacaaaag    2520
tatttacaat ttgaaaaaaa aaattaaatt aataaaattt aagattgtac aagagatttg    2580
gatctactcg cacaacattt caataataac caagtttgat tgcatagttt attagagcag    2640
tagttaaatt tttaaaagtt tttaatttta tcgtatattt tttaatttc ctcttttaaac    2700 gttgagccta caaaacctat ctaaattaaa aagttaatgg aagtgaataa ctaatctaat    2760
catcttcttt tttctcatgt tattggtatt gaatattaat taattttatt gatgattaat    2820
ccttgttaat aaatttgcta gtccaatctt aatgaaattt ttttctttca atcatatttt    2880
ttcattcata aaattcgaat tcaaaatttt atataaaaaa atcaaattca atatcattca    2940
cataaactag ttgttggtat atgccttaaa aaaaactact tgttggtata tagctaataa    3000
ctaatctaaa ctaggcccta aatacactat ttttcctaa tttaaatata gctagagtgg    3060
cggtagcgtg gccgtgtcgg ccgggcaact tacgccacta aagtcaaaag taaacgatgt    3120
aggctatact catgttattg tcttttagt ttagttttta catgtacaag tcagaagaag    3180
aatatcaatg tcgatccaca ttcaattatc ggtatacaaa tgaaagccat aaagtcaaaa    3240 tctaaaccc gtgtaattta cgcttttcta ttctagaatg ggacatactc ttcttatctc    3300
gccaagttcg tatagaaatc tgaaatttcc tttcctaaag ttcaaagtcc tagctagcat    3360
taacactata aatagacctc cctttgctc tcaatcctca accaccttgt ctatcaaaca    3420
ttataatttc tattacatac attttgtagc tagg                              3454

<210> SEQ ID NO 2
<211> LENGTH: 20
<212> TYPE: DNA
<213> ORGANISM: Glycine max

<400> SEQUENCE: 2
gagattaacg gtgcatcagg                                                 20

<210> SEQ ID NO 3
<211> LENGTH: 24
<212> TYPE: DNA
<213> ORGANISM: Glycine max

<400> SEQUENCE: 3
attaacacga gcctgaacag tact                                            24

<210> SEQ ID NO 4
<211> LENGTH: 21
<212> TYPE: DNA
<213> ORGANISM: Glycine max

<400> SEQUENCE: 4
cggtggttct atcttggcat c                                               21

<210> SEQ ID NO 5
```

```
<211> LENGTH: 22
<212> TYPE: DNA
<213> ORGANISM: Glycine max

<400> SEQUENCE: 5
gtctttcgct tcaataaccc ta                                              22

<210> SEQ ID NO 6
<211> LENGTH: 21
<212> TYPE: DNA
<213> ORGANISM: Glycine max

<400> SEQUENCE: 6
atgaatgacg gttcccatgt a                                               21

<210> SEQ ID NO 7
<211> LENGTH: 21
<212> TYPE: DNA
<213> ORGANISM: Glycine max

<400> SEQUENCE: 7
ggcattaagg cagctcactc t                                               21
```

FUNGAL RUST-INDUCIBLE PROMOTER

CROSS-REFERENCE TO RELATED APPLICATIONS

This application is a National Stage application of International Application No. PCT/US2018/032230, filed May 11, 2018, which claims priority to European Patent Application No. 17172886.8, filed May 24, 2017, contents of which are incorporated herein in their entirety.

REFERENCE TO SEQUENCE LISTING SUBMITTED VIA EFS-WEB

This application was filed electronically via EFS-Web and includes an electronically submitted sequence listing in .txt format. The .txt file contains a sequence listing entitled "13779_1556_2019-11-20_Sequence_Listing_ST25" created on Nov. 20, 2019, and is 5,926 bytes in size. The sequence listing contained in this .txt file is part of the specification and is hereby incorporated by reference in its entirety.

The present invention relates to a promoter that is induced by fungal rust. More specifically, the promoter of the invention is induced by the pathogen *Phakopsora pachyrhizi*, i.e. the Asian Soybean Rust.

BACKGROUND

Plant pathogens, including fungi, bacteria, viruses, are responsible for many diseases on cultivated crops, which can lead to significant crop losses usually considered to be between 20 to 40% of expected yields.

Rusts are plant diseases caused by fungal basidiomycete pathogens of the order Pucciniales. They are considered one of the most harmful plant pathogens in agriculture. They constitute a group of devastating plant pathogens causing enormous losses on cereal and legume crops worldwide (Brown and HovmØller, 2002, Science 297: 537-541). Their importance was highlighted in 2012, when *Puccinia* spp. infecting cereals were nominated third among the top ten fungal pathogens (Dean et al., 2012, Mol. Plant Path. 13: 414-430), Examples of economically important rust diseases include those caused by fungi of the species *Puccinia graminis* on wheat, *Puccinia striiformis* on wheat, *Uromyces phaseoli* and *Uromyces appendiculatus* on bean, or *Phakopsora pachyrhizi* on soybean.

Asian Soybean Rust is the disease caused to soybean crops (*Glycine max*) by the fungus *Phakopsora pachyrhizi*. This disease has dramatically expanded over the last years in many geographies where soybean crops are cultivated, and is causing severe losses on these crops (Hartman et al., 2011, Food Security 3: 5-17).

Many genes have been identified to be induced in soybean plants after infection by *Phakopsora pachyrhizi* (Tremblay et al., 2010, Plant Science 179: 183-193: Tremblay et al., 2011, Sequencing 2011: 1-14).

Among the genes induced in plants after infection by any fungus, chitinase genes are known (Punja et al., 1993, J. Nematology 24(4): 526-540). Chitinases are indeed considered to be part of the plant defense arsenal against fungi, in particular as enzymes having the capacity to degrade chitin, i.e. the main component of fungi's cell wall.

Plants usually have many genes encoding different isoforms of chitinases, which have been grouped in four main classes, namely Class I chitinases to Class IV chitinases (Punja et al., 1993, J. Nematology 24(4): 526-540). Some of these chitinases are expressed constitutively in the plants, and some have their expression induced by various factors. The induced chitinases have been shown to become expressed after infection by various pathogens (viruses, bacteria, fungi). Plant genes encoding chitinases have also been shown to be induced by the substrate of chitinases, chitin, i.e. the main component of fungal cell walls. These genes have also been shown to be induced by several phytohormones known to be involved in plant defense reactions, like for example ethylene, salicylic acid or jasmonic acid. Because of these various sources of induction, induction of plant chitinases is usually considered to be non-specific (Punja et al., 1993, J. Nematology 24(4): 526-540).

Among many other genes, chitinases have also been shown to be induced in soybean during infection by *Phakopsora pachyrhizi*. In particular, Tremblay et al. have reported that several genes encoding chitinase proteins are up-regulated during infection, including a Class IV chitinase, and these authors further emphasized from other studies that these genes are also induced following jasmonic acid synthesis (Tremblay et al., 2010, Plant Science 179: 183-193).

DESCRIPTION OF THE INVENTION

The present inventors have identified a promoter of a soybean chitinase gene that is surprisingly induced by fungal rusts, more specifically by the Asian Soybean Rust, *Phakopsora pachyrhizi.*

Contrary to all known plant chitinase genes, the promoter of the chitinase gene according to the invention is neither induced by chitin, or by the usual phytohormones known to be involved in plant defense. It is also not induced by wounding, and also appears not to be induced by some other fungi. The promoter according to the invention seems to be specifically induced by fungal rusts, more specifically by the Asian Soybean Rust, *Phakopsora pachyrhizi.*

In one aspect, the invention provides an isolated nucleic acid comprising fungal rust-inducible promoter activity selected from the group consisting of (a) a nucleic acid comprising a nucleotide sequence of SEQ ID NO: 1 or a functional fragment thereof; (b) a nucleic acid comprising a nucleotide sequence having at least about 95% sequence identity to SEQ ID NO: 1 or a functional fragment thereof; and (c) the nucleic acid of a functional promoter hybridizing under stringent conditions to the nucleotide sequence of SEQ ID NO: 1, or a functional fragment thereof.

SEQ ID NO: 1 represents the ca. 3.5 kbp long sequence of the promoter upstream of the translation start of a gene encoding a chitinase enzyme in the soybean plant, *Glycine max.* SEQ ID NO: 1 is a preferred promoter fragment in this invention. However, alternative functional fragments may be used. Such functional fragment would preferably be longer than 1 kbp, longer than 2 kbp, or longer than 3 kbp consecutive nucleotides upstream of the transcription start site and promote transcription of an operably linked nucleic acid preferentially in a fungal rust-inducible manner. A promoter fragment according to the invention may thus comprise a nucleotide sequence of SEQ ID No: 1 from the nucleotide at position 3400 to the nucleotide at position 3454. Alternatively, a promoter fragment according to the invention may thus comprise a nucleotide sequence of SEQ ID No: 1 from the nucleotide at position 3300 to the nucleotide at position 3454. Yet another promoter fragment according to the invention may thus comprise a nucleotide sequence of SEQ ID No: 1 from the nucleotide at position 3200 to the nucleotide at position 3454. Still another promoter fragment according to the invention may thus comprise a nucleotide sequence of SEQ ID No: 1 from the nucleotide at position 3100 to the nucleotide at position 3454. Yet another promoter fragment according to the invention may thus comprise a nucleotide sequence of SEQ ID No: 1 from the nucleotide at position 3000 to the nucleotide at position 3454. Another promoter fragment according to the invention may thus comprise a nucleotide sequence of SEQ ID No: 1 from the nucleotide at position 2500 to the nucleotide at position 3454. Yet another promoter fragment according to the invention may thus comprise a nucleotide sequence of SEQ ID No: 1 from the nucleotide at position 2000 to the nucleotide at position 3454. Still another promoter fragment according to the invention may thus comprise a nucleotide sequence of SEQ ID No: 1 from the nucleotide at position 1500 to the nucleotide at position 3454. Yet another promoter fragment according to the invention may thus comprise a nucleotide sequence of SEQ ID No: 1 from the nucleotide at position 1000 to the nucleotide at position 3454. A further promoter fragment according to the invention may thus comprise a nucleotide sequence of SEQ ID No: 1 from the nucleotide at position 500 to the nucleotide at position 3454.

The nucleic acid comprising the fungal rust-inducible promoter activity according to the invention may also be comprised in a larger DNA molecule.

According to the invention, the promoter nucleic acid has fungal rust-inducible activity. "Fungal rust-inducible promoter activity" means that the promoter activity is at least 2 times, or at least 5 times, or at least 10 times, or at least 20 times or even at least 100 times higher when the plant or plant part is subjected to infection by a fungal rust than in control condition. In other words, in fungal rust-inducible promoter activity, transcription of the nucleic acid operably linked to the promoter of the invention is at least 2 times, or at least 5 times, or at least 10 times, or at least 20 times or even at least 100 times higher when the plant or plant part is subjected to a fungal rust infection than in control condition. In other words, the fungal rust-inducible promoter controls expression of the nucleic acid operably linked to it.

According to a preferred embodiment, the promoter nucleic acid according to the invention also has fungal rust-specific promoter activity. "Fungal rust-specific promoter activity" means that the activity of the promoter is specifically induced by a fungal rust, and by no other elements or groups of fungi.

According to another embodiment, the fungal rust-inducible activity of the promoter nucleic acid according to the invention is a local inducibility at the point of infection. Preferably, this local inducibility has no systemic effect, i.e. does not spread within the plant beyond the point of infection by the fungal rust.

The "fungal rust" capable of inducing, preferably specifically, the promoter according to the invention is preferably the fungus *Phakopsora pachyrhizi.*

As used herein, "promoter" or "functional promoter" means a region of DNA sequence that is essential for the initiation of transcription of DNA, resulting in the generation of an RNA molecule that is complementary to the transcribed DNA; this region may also be referred to as a "5' regulatory region". Promoters are usually located upstream of the coding sequence to be transcribed and have regions that act as binding sites for RNA polymerase II and other proteins such as transcription factors (trans-acting protein factors that regulate transcription) to initiate transcription of an operably linked gene. Promoters may themselves contain sub-elements (i.e. promoter motifs) such as cis-elements or enhancer domains that regulate the transcription of operably linked genes. The promoters of this invention may be altered to contain "enhancer DNA" to assist in elevating gene expression. As is known in the art, certain DNA elements can be used to enhance the transcription of DNA. These enhancers often are found 5' to the start of transcription in a promoter that functions in eukaryotic cells, but can often be inserted upstream (5') or downstream (3') to the coding sequence. In some instances, these 5' enhancer DNA elements are introns. Among the introns that are useful as enhancer DNA are the 5' introns from the rice actin 1 gene (see U.S. Pat. No. 5,641,876), the rice actin 2 gene, the maize alcohol dehydrogenase gene, the maize heat shock protein 70 gene (see U.S. Pat. No. 5,593,874), the maize shrunken 1 gene, the light sensitive 1 gene of *Solanum tuberosum*, the *Arabidopsis* histone 4 intron and the heat shock protein 70 gene of *Petunia hybrida* (see U.S. Pat. No. 5,659,122). A preferred enhancer element according to the invention is the transcription activator of the tobacco etch virus (TEV) described by Carrington & Freed (1990, J. Virol. 64(4)1590-7). Thus, as contemplated herein, a promoter or promoter region includes variations of promoters derived by inserting or deleting regulatory regions, subjecting the promoter to random or site-directed mutagenesis, etc. The activity or strength of a promoter may be measured in terms of the amounts of RNA it produces, or the amount of protein accumulation in a cell or tissue, relative to a promoter whose transcriptional activity has been previously assessed.

A "functional fragment" of a promoter according to the invention shall at least have both the functionality of a promoter, and the functionality of being specifically induced by a fungal rust. Promoter activity for a functional promoter fragment under fungal rust infection may be determined by those skilled in the art, for example using analysis of RNA accumulation produced from the nucleic acid which is operably linked to the promoter as described herein, whereby the nucleic acid which is operably linked to the promoter can be the nucleic acid which is naturally linked to the promoter, i.e. the endogenous gene of which expression is controlled by the promoter.

The RNA accumulation, or levels of RNA, such as mRNA, can be measured either at a single time point or at multiple time points and as such the fold increase can be an average fold increase or an extrapolated value derived from experimentally measured values. As it is a comparison of levels, any method that measures mRNA levels can be used. In a preferred aspect, the tissue or organs compared are leaf tissues.

The fungal rust-inducible expression capacity of the identified or generated fragment of the promoter can also be conveniently tested by operably linking such DNA molecules to another DNA molecule encoding an easily scorable marker, such as e.g. a beta-glucuronidase (GUS) gene, introducing such a recombinant gene into a plant and analyzing the expression pattern of the marker in the plant, e.g., the leaves, as compared with the expression pattern of the marker in a control plant. Other candidates for a marker (or a reporter gene) are chloramphenicol acetyl transferase (CAT) and proteins with fluorescent properties, such as green fluorescent protein (GFP) from *Aequora victoria.* To define a minimal promoter region, a DNA segment representing the promoter region is removed from the 5 region of the gene of interest and operably linked to the coding sequence of a marker (reporter) gene by recombinant DNA techniques well known to the art. The reporter gene is linked downstream of the promoter, so that transcripts initiating at the promoter proceed through the reporter gene. Reporter genes generally encode proteins, which are easily measured, including, but not limited to, chloramphenicol acetyl transferase (CAT), beta-glucuronidase (GUS), green fluorescent protein (GFP), beta-galactosidase (beta-GAL), and luciferase. The expression cassette containing the reporter gene under the control of the promoter can be introduced into an appropriate cell type by transfection techniques well known to the art. To assay for the reporter protein, cell lysates are prepared and appropriate assays, which are well known in the art, for the reporter protein are performed. The level of enzyme activity corresponds to the amount of enzyme that was made, which in turn reveals the level of expression and the fungal rust-specific functionality from the promoter or promoter fragment of interest. This level of expression can also be compared to other promoters to determine the relative strength of the promoter under study. Once activity and functionality is confirmed, additional mutational and/or deletion analyses may be employed to determine the minimal region and/or sequences required to initiate transcription. Thus, sequences can be deleted at the 5' end of the promoter region and/or at the 3' end of the promoter region, and nucleotide substitutions introduced. These constructs are then again introduced in cells and their activity and/or functionality determined.

It will herein further be clear that equivalent, i.e. orthologous, fungal rust-inducible promoters can be isolated from other plants than *Glycine max*, that are also known to be hosts of the pathogen *Phakopsora pachyrhizi*, such as for example other plants of the Fabaceae family, like e.g. *Cajanus cajan, Lupinus* sp., *Phaseolus vulgaris* or *Vigna unquiculata*. To this end, orthologous promoter fragments may be isolated from other plants using SEQ ID NO: 1 or a functional fragment having at least 600 consecutive nucleotides thereof as a probe and identifying nucleotide sequences from these other plants which hybridize under the herein described hybridization conditions. By way of example, a promoter of the invention may be used to screen a genomic library of a crop or plant of interest to isolate corresponding promoter sequences according to techniques well known in the art. Thus, a promoter sequence of the invention may be used as a probe for hybridization with a genomic library under medium to high stringency conditions. As an alternative, equivalent promoters can be isolated using the coding sequences of the genes controlled by the promoters of SEQ ID NO: 1, i.e. chitinases, to screen a genomic library (e.g. by hybridization or in silico) of a crop of interest. When sufficient identity between the coding sequences is obtained (for example, higher than 95%>identity), promoter regions can be isolated upstream of the orthologous genes.

Suitable to the invention are nucleic acids comprising fungal rust-inducible promoter activity which comprise a nucleotide sequence having at least 95%, at least 98% or at least 99% sequence identity to the herein described promoters and promoter regions or functional fragments thereof and are also referred to as variants. The term "variant" with respect to the transcription regulating nucleotide sequence SEQ ID NO: 1 of the invention is intended to mean substantially identical sequences. Naturally occurring allelic variants such as these can be identified with the use of well-known molecular biology techniques, as, for example, with polymerase chain reaction (PCR) and hybridization techniques as herein outlined before. Variant nucleotide sequences also include synthetically derived nucleotide sequences, such as those generated, for example, by using site-directed mutagenesis of SEQ ID NO: 1. Generally, nucleotide sequence variants of the invention will have generally at least 95%, i.e. 96%, 97%, 98% or 99% nucleotide sequence identity to SEQ ID NO:1 or a functional fragment thereof. Derivatives of the DNA molecules disclosed herein may include, but are not limited to, deletions of sequence, single or multiple point mutations, alterations at a particular restriction enzyme site, addition of functional elements, or other means of molecular modification which may enhance, or otherwise alter promoter expression. Techniques for obtaining such derivatives are well-known in the art (see, for example, J. F. Sambrook, D. W. Russell, and N. Irwin (2000) Molecular Cloning: A Laboratory Manual, $3^{rd}$ edition Volumes 1, 2, and 3. Cold Spring Harbor Laboratory Press). For example, one of ordinary skill in the art may delimit the functional elements within the promoters disclosed herein and delete any non-essential elements. Functional elements may be modified or combined to increase the utility or expression of the sequences of the invention for any particular application. Those of skill in the art are familiar with the standard resource materials that describe specific conditions and procedures for the construction, manipulation, and isolation of macromolecules (e.g., DNA molecules, plasmids, etc.), as well as the generation of recombinant organisms and the screening and isolation of DNA molecules.

In accordance with the present invention, the term "sequence identity" is to be understood as the number of nucleotides of a polynucleotide that are identical to the nucleotides of another polynucleotide, expressed as a percentage of the total number of nucleotides of a considered length of such polynucleotides. Sequence identity is preferably determined by comparing the sequences of the polynucleotides of the present invention with other polynucleotides using appropriate sequence alignment computer programs based on global or local alignment algorithms. If the polynucleotides that are compared have different lengths, the percentage of sequence identity is to be determined in such a way that the number of respectively nucleotides of the shorter sequence that are in common with the longer sequence, determines the length over which the percentage of sequence identity is determined. These computer programs usually use the Needleman and Wunsch global alignment algorithm to align two sequences over their entire length, maximizing the number of matches and minimizing the number of gaps. Generally, the default parameters are used, with a gap creation penalty=10 and gap extension penalty=0.5 (both for nucleotide and protein alignments). Preferably, identity is determined by means of the computer program ClustalW, which is well known and available to the public (Thompson et al., 1994, Nucleic Acids Research 22, 4673-4680). ClustalW is made publicly available on world wide web at ebi.ac.ukitoolsiclustalW2/index.html.

Preferably, Version 2.1 of the ClustalW computer program is used to determine the identity between the nucleotide sequence of the nucleic acid molecules according to the invention, for example, and the nucleotide sequence of other nucleic acid molecules. In doing so, the following parameters must be set: KTUPLE=2, TOPDIAGS=4, PAIRGAP=5, DNAMATRIX:IUB, GAPOPEN=10, GAPEXT=5, MAXDIV=40, TRANSITIONS: unweighted.

According to the present invention, the term 'hybridizing under stringent conditions" refers to conditions under which a polynucleotide hybridizes (usually designed as a probe) to another one with a detectably greater degree than to other polynucleotides (e.g., at least 2-fold over background). Stringent conditions are sequence-dependent and differ according to circumstances. By controlling the stringency of the hybridization and/or washing conditions, polynucleotides that are 100% identical in sequence to a polynucleotide probe can be identified (homologous probing). Alternatively, stringency conditions can be adjusted to allow some mismatching in sequences so that polynucleotides with lower degrees of sequence identity are detected (heterologous probing). Generally, a polynucleotide probe is less than about 1000 nucleotides in length, preferably less than 500 nucleotides in length.

Generally, stringent conditions are selected to be about 5° C. lower than the thermal melting point (Tm) for the specific sequences at a defined ionic strength and pH. The Tm is the temperature (under defined ionic strength and pH) at which 50% of the target sequence hybridizes to a perfectly matching probe. Typically stringent conditions will be chosen in which the salt concentration is about 0.02 molar at pH 7 and the temperature is at least 60° C. Lowering the salt concentration and/or increasing the temperature increases stringency. Stringent conditions for RNA-DNA hybridizations (Northern blots using a probe of e.g. 100 nt) are for example those which include at least one wash in 0.2×SSC at 63° C. for 20 min, or equivalent conditions. Stringent conditions for DNA-DNA hybridization (Southern blots using a probe of e.g. 100 nt) are for example those which include at least one wash (usually 2) in 0.2×SSC at a temperature of at least 50° C., usually about 55° C., for 20 min, or equivalent conditions. See also Sambrook et al. (1989) Molecular Cloning: A Laboratory Manual, Second Edition, Cold Spring Harbor Laboratory Press, and Sambrook and Russell (2001) Molecular Cloning: A Laboratory Manual, Third Edition, Cold Spring Harbor Laboratory Press, NY; and in Volumes 1 and 2 of Ausubel et al. (1994) Current Protocols in Molecular Biology, Current Protocols, USA.

A "functional fragment" of a nucleic acid comprising fungal rust-inducible promoter activity denotes a nucleic acid comprising a stretch of the nucleic acid sequences of SEQ ID NO: 1, or of the nucleic acid having at least 95% sequence identity to SEQ ID NO: 1, which is at least 50 bp and still exerts the desired function, i.e. which has fungal rust-inducible promoter activity. Assays for determining fungal rust-inducible promoter activity are provided herein. Preferably, a functional fragment of the fungal rust-inducible promoter contains the conserved promoter motifs, such as, for example, conserved promoter motifs as described in DoOP (doop.abc.hu, databases of Orthologous Promoters, Barta E. et al. (2005) Nucleic Acids Research Vol. 33, D86-D90). A functional fragment may be a fragment of at least about 50 pb, at least about 100 bp, at least about 200 bp, at least about 300 bp, at least about 400 bp, at least about 500 bp from the transcription start site or at least about 1000 bp, at least about 1500 bp, at least about 2000 bp, at least about 2500 bp, at least about 3000 bp from the translation start site.

A functional fragment according to the invention can also be a combination of functional fragment, i.e. a functional fragment can comprise two or more fragments of the promoter nucleic acid according to the invention. For example, a functional fragment can comprise, alternatively consists of, operably linked, one fragment of the promoter nucleic acid according to the invention having the transcription activation functionality, and one other fragment of the promoter nucleic acid according to the invention having the fungal rust induction functionality.

The promoters according to the invention can further be used to create hybrid promoters, i.e. promoters containing (parts of) one or more of the promoters(s) of the current invention and (parts of) other promoter which can be newly identified or known in the art. Such hybrid promoters may have optimized tissue specificity or expression level.

A further embodiment provides a recombinant gene comprising the nucleic acid having fungal rust-induced promoter activity described above, operably linked to a heterologous nucleic acid sequence encoding an expression product of interest, and optionally a transcription termination and polyadenylation sequence, preferably a transcription termination and polyadenylation region functional in plant cells.

The term "recombinant gene" refers to any artificial gene that contains: a) DNA sequences, including regulatory and coding sequences that are not found together in nature, or b) sequences encoding parts of proteins not naturally adjoined, or c) parts of promoters that are not naturally adjoined. Accordingly, a recombinant gene may comprise regulatory sequences and coding sequences that are derived from different sources, or comprise regulatory sequences, and coding sequences derived from the same source, but arranged in a manner different from that found in nature.

The term "heterologous" refers to the relationship between two or more nucleic acid sequences that are derived from different sources. For example, a promoter is heterologous with respect to an operably linked DNA region, such as a coding sequence if such a combination is not normally found in nature. In addition, a particular sequence may be "heterologous" with respect to a cell or organism into which it is inserted (i.e. does not naturally occur in that particular cell or organism). For example, the recombinant gene disclosed herein is a heterologous nucleic acid.

The term "operably linked" means that genetic elements of the recombinant gene are linked to one another in such a way that their function is coordinated and allows the expression of the coding sequence. By way of example, a promoter is functionally linked to a coding sequence when it is capable of ensuring the expression of said coding sequence, i.e. its transcription into a RNA molecule, whether an mRNA (then coding for a protein) or any other type of RNA (e.g. a dsRNA). The construction of a recombinant gene according to the invention and the assembly of its various elements can be carried out using techniques well known to those skilled in the art, in particular those described in Sambrook et al. (2001, Molecular Cloning: A Laboratory Manual, Third Edition, Cold Spring Harbor Laboratory Press, NY). "Functionally linked" is an equivalent term.

The term "expression product" refers to a product of transcription. Said expression product can be the transcribed RNA. It is understood that the RNA which is produced is a biologically active RNA. Said expression product can also be a peptide, a polypeptide, or a protein, when said biologically active RNA is an mRNA and said protein is produced by translation of said mRNA.

As an example, the promoter according to the invention can be used to drive the expression of an expression product imparting cell death, like e.g. the combined use of the barnase and barstar enzymes. Preferably, the promoter according to the invention is used to drive the expression of the barnase enzyme in plants transformed with a second recombinant gene comprising a constitutive promoter operably linked to the barstar protein.

Alternatively, the heterologous nucleic acid, operably linked to the promoters of the invention, may also code for an RNA capable of modulating the expression of a gene. Said RNA capable of modulating the expression of a gene can be an RNA which reduces expression of a gene. Said RNA can reduce the expression of a gene for example through the mechanism of RNA-mediated gene silencing.

Said RNA capable of modulating the expression of a gene can be a silencing RNA down-regulating expression of a target gene. As used herein, "silencing RNA" or "silencing RNA molecule" refers to any RNA molecule, which upon introduction into a plant cell, reduces the expression of a target gene. Such silencing RNA may e.g. be so-called "antisense RNA", whereby the RNA molecule comprises a sequence of at least 20 consecutive nucleotides having 95% sequence identity to the complement of the sequence of the target nucleic acid, preferably the coding sequence of the target gene. However, antisense RNA may also be directed to regulatory sequences of target genes, including the promoter sequences and transcription termination and polyadenylation signals. Silencing RNA further includes so-called "sense RNA" whereby the RNA molecule comprises a sequence of at least 20 consecutive nucleotides having 95% sequence identity to the sequence of the target nucleic acid. Other silencing RNA may be "unpolyadenylated RNA" comprising at least 20 consecutive nucleotides having 95%>sequence identity to the complement of the sequence of the target nucleic acid, such as described in WO01/12824 or U.S. Pat. No. 6,423,885 (both documents herein incorporated by reference). Yet another type of silencing RNA is an RNA molecule as described in WO03/076619 (herein incorporated by reference) comprising at least 20 consecutive nucleotides having 95%>sequence identity to the sequence of the target nucleic acid or the complement thereof, and further comprising a largely-double stranded region as described in WO03/076619 (including largely double stranded regions comprising a nuclear localization signal from a viroid of the Potato spindle tuber viroid-type or comprising CUG trinucleotide repeats). Silencing RNA may also be double stranded RNA comprising a sense and antisense strand as herein defined, wherein the sense and antisense strand are capable of base-pairing with each other to form a double stranded RNA region (preferably the said at least 20 consecutive nucleotides of the sense and antisense RNA are complementary to each other). The sense and antisense region may also be present within one RNA molecule such that a hairpin RNA (hpRNA) can be formed when the sense and antisense region form a double stranded RNA region. hpRNA is well-known within the art (see e.g WO99153050, herein incorporated by reference). The hpRNA may be classified as long hpRNA, having long, sense and antisense regions which can be largely complementary, but need not be entirely complementary (typically larger than about 200 bp, ranging between 200-1000 bp). hpRNA can also be rather small ranging in size from about 30 to about 42 bp, but not much longer than 94 bp (see WO04/073390, herein incorporated by reference). Silencing RNA may also be artificial micro-RNA molecules as described e.g. in WO2005/052170, WO2005/047505 or US 2005/0144667, or ta-siRNAs as described in WO2006/074400 (all documents incorporated herein by reference). Said RNA capable of modulating the expression of a gene can also be an RNA ribozyme.

Said RNA capable of modulating the expression of a gene can modulate, preferably down-regulate, the expression of other genes (i.e. target genes), e.g. present within a pathogen that infects the transgenic plant.

The nucleic acid sequence heterologous to the promoters according to the invention may generally be any nucleic acid sequence effecting increased, altered (e.g. in a different organ) or reduced level of transcription of a gene for which such expression modulation is desired. The nucleic acid sequence can for example encode a protein of interest.

A "transcription termination and polyadenylation region" as used herein is a sequence that controls the cleavage of the nascent RNA, whereafter a poly(A) tail is added at the resulting RNA 3' end, functional in plant cells. Transcription termination and polyadenylation signals functional in plant cells include, hut are not limited to, 3'nos, 3'35S, 3'his and 3'g7.

Any of the promoters and heterologous nucleic acid sequences described above may be provided in a recombinant vector. A recombinant vector typically comprises, in a 5' to 3' orientation: a promoter to direct the transcription of a nucleic acid sequence and a nucleic acid sequence. The recombinant vector may further comprise a 3' transcriptional terminator, a 3' polyadenylation signal, other untranslated nucleic acid sequences, transit and targeting nucleic acid sequences, selectable markers, enhancers, and operators, as desired. The wording "5' UTR" refers to the untranslated region of DNA upstream, or 5' of the coding region of a gene and "3' UTR" refers to the untranslated region of DNA downstream, or 3' of the coding region of a gene. Means for preparing recombinant vectors are well known in the art. Methods for making recombinant vectors particularly suited to plant transformation are described in U.S. Pat. Nos. 4,971,908, 4,940,835, 4,769,061 and 4,757,011. Typical vectors useful for expression of nucleic acids in higher plants are well known in the art and include vectors derived from the tumor-inducing (Ti) plasmid of *Agrobacterium tumefaciens*.

The recombinant vector may also contain one or more additional nucleic acid sequences. These additional nucleic acid sequences may generally be any sequences suitable for use in a recombinant vector. Such nucleic acid sequences include, without limitation, any of the nucleic acid sequences, and modified forms thereof, described above. The additional structural nucleic acid sequences may also be operably linked to any of the above described promoters. The one or more structural nucleic acid sequences may each be operably linked to separate promoters. Alternatively, the structural nucleic acid sequences may be operably linked to a single promoter (i.e. a single operon).

Yet other embodiments provide a host cell, such as an *E. coli* cell, an *Agrobacterium* cell, a yeast cell, or a plant cell, comprising the isolated nucleic acid according to the invention, or the recombinant genes according to the invention.

Other nucleic acid sequences may also be introduced into the host cell along with the promoter and structural nucleic acid sequence, e. g. also in connection with the vector of the invention. These other sequences may include 3' transcriptional terminators, 3' polyadenylation signals, other untranslated nucleic acid sequences, transit or targeting sequences, selectable markers, enhancers, and operators. Preferred nucleic acid sequences of the present invention, including recombinant vectors, structural nucleic acid sequences, promoters, and other regulatory elements, are described above.

In further embodiments, a plant is provided comprising any of the nucleic acids or recombinant genes according to the invention. A further embodiment provides plant parts and seeds obtainable from the plant according to the invention. These plant parts and seeds comprise the recombinant genes described above. In another embodiment, the plants, plant parts or seeds according to the invention are cotton, soybean or wheat plants, plant parts or seeds.

The plant cell or plant comprising any of the recombinant gene according to the invention can be a plant cell or a plant comprising a recombinant gene of which either the promoter, or the heterologous nucleic acid sequence operably linked to said promoter, are heterologous with respect to the plant cell. Such plant cells or plants may be transgenic plant in which the recombinant gene is introduced via transformation. Alternatively, the plant cell of plant may comprise the promoter according to the invention derived from the same species operably linked to a nucleic acid which is also derived from the same species, i.e. neither the promoter nor the operably linked nucleic acid is heterologous with respect to the plant cell, but the promoter is operably linked to a nucleic acid to which it is not linked in nature. A recombinant gene can be introduced in the plant or plant cell via transformation, such that both the promoter and the operably linked nucleotide are at a position in the genome in which they do not occur naturally. Alternatively, the promoter according to the invention can be integrated in a targeted manner in the genome of the plant or plant cell upstream of an endogenous nucleic acid encoding an expression product of interest, i.e. to modulate the expression pattern of an endogenous gene. The promoter that is integrated in a targeted manner upstream of an endogenous nucleic acid can be integrated in cells of a plant species from which it is originally derived, or in cells of a heterologous plant species. Alternatively, a heterologous nucleic acid can be integrated in a targeted manner in the genome of the plant or plant cell downstream of the promoter according to the invention, such that said heterologous nucleic acid is expressed upon fungal rust infection. Said heterologous nucleic acid is a nucleic acid which is heterologous with respect to the promoter, i.e. the combination of the promoter with said heterologous nucleic acid is not normally found in nature. Said heterologous nucleic acid may be a nucleic acid which is heterologous to said plant species in which it is inserted, but it may also naturally occur in said plant species at a different location in the plant genome. Said promoter or said heterologous nucleic acid can be integrated in a targeted manner in the plant genome via targeted sequence insertion, using, for example, the methods as described in WO2005/049842.

"Plants" encompasses "monocotyledonous plants" and "dicotyledonous plants".

"Monocotyledonous plants", also known as "monocot plants" or "monocots" are well known in the art and are plants of which the seed typically has one cotyledon. Examples of monocotyledons plants are grasses, such as meadow grass (blue grass, Poa), forage grass such as festuca, lolium, temperate grass, such as Agrostis, and cereals, e.g., wheat, oats, rye, barley, rice, sorghum, and maize (corn).

"Dicotyledonous plants", also known as "dicot plants" or "dicots" are well known in the art and are plants of which the seed typically has two cotyledons. Examples of families of dicotyledonous plants are Brassicaceae, Solanaceae, Fabaceae, Malvaceae. A preferred dicotyledonous plant is soybean (*Glycine max*).

"Plant parts" as used herein are parts of the plant, which can be cells, tissues or organs, such as seeds, severed parts such as roots, leaves, flowers, pollen, fibers etc.

The plants or seeds of the plants according to the invention may be further treated with a chemical compound, such as a chemical compound selected from the following lists: Herbicides: Diuron, Fluometuron, MSMA, Oxyfluorfen, Prometryn, Trifluralin, Carfentrazone, Clethodim, Fluazifop-butyl, Glyphosate, Norflurazon, Pendimethalin, Pyrithiobac-sodium, Trifloxysulfuron, Tepraloxydim, Glufosinate, Flumioxazin, Thidiazuron; cotton insecticides such as Acephate, Aldicarb, Chlorpyrifos, Cypermethrin, Deltamethrin, Abamectin, Acetamiprid, Emamectin Benzoate, Imidacloprid, Indoxacarb, Lambda-Cyhalothrin, Spinosad, Thiodicarb, Gamma-Cyhalothrin, Spiromesifen, Pyridalyl, Flonicamid, Flubendiamide, Triflumuron, Rynaxypyr, Beta-Cyfluthrin, Spirotetramat, Clothianidin, Thiamethoxam, Thiacloprid, Dinetofuran, Flubendiamide, Cyazypyr, Spinosad, Spinotoram, gamma Cyhalothrin, 4-[[(6-Chlorpyridin-3-yl)methyl](2,2-difluorethyl)amino]furan-2(5H)-on, Thiodicarb, Avermectin, Flonicamid, Pyridalyl, Spiromesifen, Sulfoxaflor; and cotton fungicides such as Azoxystrobin, Bixafen, Boscalid, Carbendazim, Chlorothalonil, Copper, Cyproconazole, Difenoconazole, Dimoxystrobin, Epoxiconazole, Fenamidone, Fluazinam, Fluopyram, Fluoxastrobin, Fluxapyroxad, Iprodione, Isopyrazam, Isotianil, Mancozeb, Maneb, Metominostrobin, Penthiopyrad, Picoxystrobin, Propineb, Prothioconazole, Pyraclostrobin, Quintozene, Tebuconazole, Tetraconazole, Thiophanate-methyl, Trifloxystrobin, Clopyralid, Diclofop, Ethametsulfuron, Fluazifop, Metazachlor, Quinrnerac, Quizalofop, Fungicides/PGRs; Azoxystrobin, N-[9-(dichloromethylene)-1,2,3,4-tetrahydro-1,4-methanonaphthalen-5-yl]-3-(difluoromethyl)-1-methyl-1H-pyrazole-4-carboxamide (Benzovindiflupyr, Benzodiflupyr), Bixafen, Boscalid, Carbendazim, Carboxin, Chlormequat-chloride, Coniothryrium minitans, Cyproconazole, Cyprodinil, Difenoconazole, Dirnethomorph, Dirnoxystrobin, Epoxiconazole, Famoxadone, Fluazinam, Fludioxonil, Fluopicolide, Fluopyram, Fluoxastrobin, Fluquinconazole, Flusilazole, Fluthianil, Flutriafol, Fluxapyroxad, Iprodione, Isopyrazam, Mefenoxam, Mepiquat-chloride, Metalaxyl, Metconazole, Metominostrobin, Paclobutrazole, Penflufen, Penthiopyrad, Picoxystrobin, Prochloraz, Prothioconazole, Pyraclostrobin, Sedaxane, Tebuconazole, Tetraconazole, Thiophanate-methyl, Thiram, Triadimenol, Trifloxystrobin, *Bacillus firmus*, *Bacillus firmus* strain 1-1582, *Bacillus subtilis*, *Bacillus subtilis* strain GB03, *Bacillus subtilis* strain QST 713, *Bacillus pumulis*, *Bacillus*, *pumulis* strain GB34. Insecticides: Acetamiprid, Aidicarb, Azadirachtin, Carbofuren, Chlorantraniliprole (Rynaxypyr), Clothianidin, Cyantraniliprole (Cyazypyr), (beta-)Cyfluthrin, gamma-Cyhalothrin, lambda-Cyhalothrin, Cypermethrin, Deltamethrin, Dimethoate, Dinetofuran, Ethiprole, Flonicamid, Flubendiamide, Fluensulfone, Fluopyram, Flupyradilurone, tau-Fluvalinate, Imicyafos, Imidacloprid, Metaflumizone, Methiocarb, Pymetrozine, Pyrifluguinazon, Spinetoram, Spinosad, Spirotetramate, Sulfoxaflor, Thiacloprid, Thiamethoxam, I-(3-chloropyridin-2-yl)-N-[4-cyano-2-methyl-6-(methylcarbamoyl)phenyl]-3-{[5-(trifluoromethyl)-2H-tetrazol-2-yl]methyl}-1H-pyrazole-5-carboxamide, 1-(3-chloropyridin-2-yl)-N-[4-cyano-2-methyl-6-(methylcarbarnoyl)phenyl]-3-{[5-(trifluoromethyl)-1H-tetrazol-1-yl]methyl}-1H-pyrazole-5-carboxamide, 1-{2-fluoro-4-methyl-5-[(2,2,2-trifluoroethyl)sulfinyl]phen (IE)-N-[(6-chloropyridin-3-yl)methyl]-N'-cyano-N-(2,2-difluoroethyl)etlianimidamide, *Bacillus firmus*, *Bacillus firmus* strain 1-1582, *Bacillus subtilis*, *Bacillus subtilis* strain GB03, *Bacillus subtilis* strain QST 713, Metarhizium anisopliae F52.

Whenever reference to a "plant" or "plants" according to the invention is made, it is understood that also plant parts (cells, tissues or organs, seed pods, seeds, severed parts such as roots, leaves, flowers, pollen, etc.), progeny of the plants which retain the distinguishing characteristics of the parents, such as seed obtained by selfing or crossing, e.g. hybrid seed (obtained by crossing two inbred parental lines), hybrid plants and plant parts derived there from are encompassed herein, unless otherwise indicated.

In some embodiments, the plant cells of the invention as well as plant cells generated according to the methods of the invention, may be non-propagating cells.

The obtained plants according to the invention can be used in a conventional breeding scheme to produce more plants with the same characteristics or to introduce the same characteristic in other varieties al the same or related plant species, or in hybrid plants. The obtained plants can further be used for creating propagating material. Plants according to the invention can further be used to produce gametes, seeds (including crushed seeds and seed cakes), seed oil, fibers, yarn, embryos, either zygotic or somatic, progeny or hybrids of plants obtained by methods of the invention, Seeds obtained from the plants according to the invention are also encompassed by the invention.

"Creating propagating material", as used herein, relates to any means know in the art to produce further plants, plant parts or seeds and includes inter alia vegetative reproduction methods (e.g. air or ground layering, division, (bud) grafting, micropropagation, stolons or runners, storage organs such as bulbs, corms, tubers and rhizomes, striking or cutting, twin-scaling), sexual reproduction (crossing with another plant) and asexual reproduction (e.g. apomixis, somatic hybridization).

Yet other embodiments provide a method of producing a transgenic plant comprising the steps of (a) introducing or providing any of the recombinant genes according to the invention to a plant cell to create transgenic cells; and (b) regenerating transgenic plants from said transgenic cell.

"Introducing" in connection with the present application relates to the placing of genetic information in a plant cell or plant by artificial means. This can be effected by any method known in the art for introducing RNA or DNA into plant cells, protoplasts, calli, roots, tubers, seeds, stems, leaves, seedlings, embryos, pollen and microspores, other plant tissues, or whole plants. "Introducing" also comprises stably integrating into the plant's genome. Introducing the recombinant gene can be performed by transformation or by crossing with a plant obtained by transformation or its descendant (also referred to as "introgression").

The term "providing" may refer to introduction of an exogenous DNA molecule to a plant cell by transformation, optionally followed by regeneration of a plant from the transformed plant cell. The term may also refer to introduction of the recombinant DNA molecule by crossing of a transgenic plant comprising the recombinant DNA molecule with another plant and selecting progeny plants which have inherited the recombinant DNA molecule or transgene. Yet another alternative meaning of providing refers to introduction of the recombinant DNA molecule by techniques such as protoplast fusion, optionally followed by regeneration of a plant from the fused protoplasts.

The recombinant gene may be introduced into a plant cell by methods well-known in the art.

The term "transformation" herein refers to the introduction (or transfer) of nucleic acid into a recipient host such as a plant or any plant parts or tissues including plant cells, protoplasts, calli, roots, tubers, seeds, stems, leaves, fibers, seedlings, embryos and pollen. Plants containing the transformed nucleic acid sequence are referred to as "transgenic plants".

Transformed, transgenic and recombinant refer to a host organism such as a plant into which a heterologous nucleic acid molecule (e.g. an expression cassette or a recombinant vector) has been introduced. The nucleic acid can be stably integrated into the genome of the plant.

As used herein, the phrase "transgenic plant" refers to a plant having a nucleic acid stably integrated into a genome of the plant, for example, the nuclear or plastid genomes. In other words, plants containing transformed nucleic acid sequence are referred to as "transgenic plants" and includes plants directly obtained from transformation and their descendants (Tx generations). Transgenic and recombinant refer to a host organism such as a plant into which a heterologous nucleic acid molecule (e.g. the promoter, the recombinant gene or the vector as described herein) has been introduced. The nucleic acid can be stably integrated into the genome of the plant.

To obtain the cells or plants according to the invention, those skilled in the art can use one of the numerous known methods of transformation.

One of these methods consists in bringing the cells or tissues of the host organisms to be transformed into contact with polyethylene glycol (PEG) and the vectors of the invention (Chang and Cohen, 1979, Mol. Gen. Genet. 168: 111-115; Mercenier and Chassy, 1988, Biochimie 70: 503-517). Electroporation is another method, which consists in subjecting the cells or tissues to be transformed and the vectors of the invention to an electric field (Andreason and Evans, 1988, Biotechniques 6: 650-660; Shigekawa and Dower, 1989, Aust. J. Biotechnol. 3: 56-62). Another method consists in directly injecting the vectors into the cells or the tissues by microinjection (Gordon and Ruddle, 1985, Gene 33: 121-136). Advantageously, the "biolistic" method may be used. It consists in bombarding cells or tissues with particles onto which the vectors of the invention are adsorbed (Bruce et al., 1989, Proc. Natl. Acad. Sci. USA 86: 9692-9696: Klein et al., 1992, Biotechnology 10: 286-291; U.S. Pat. No. 4,945,050). Preferably, the transformation of plant cells or tissues can be carried out using bacteria of the *Agrobacterium* genus, preferably by infection of the cells or tissues of said plants with *A. tumefaciens* (Knopf, 1979, Subcell. Biochem. 6: 143-173; Shaw et al., 1983, Gene 23: 315-330) or *A. rhizogenes* (Bevan and Chilton, 1982. Anon. Rev. Genet. 16: 357-384; Tepfer and Casse-Delbart, 1987, Microbiol, Sci. 4: 24-28). Preferably, the transformation of plant cells or tissues with *Agrobacterium tumefaciens* is carried out according to the protocol described by Hiei et al., (1994, Plant J. 6: 271-282). Those skilled in the art will choose the appropriate method according to the nature of the host organisms to be transformed.

The recombinant DNA molecules according to the invention may be introduced into plants in a stable manner or in a transient manner using methods well known in the art. The recombinant genes may be introduced into plants, or may be generated inside the plant cell as described e.g. in EP 1339859.

Further provided are methods of effecting fungal rust-inducible expression of a nucleic acid, comprising introducing a recombinant gene according to the invention that comprise a promoter having fungal rust-inducible promoter activity into the genome of a plant, or providing the plant according to the invention. Also provided is a method for altering biotic or abiotic stress tolerance, root architecture, nutrient use efficiency, nematode resistance or yield of a plant, comprising introducing the recombinant gene according to the invention into the genome of a plant, or providing the plant according to the invention.

Also provided is the use of the isolated nucleic acid according to the invention to regulate expression of an operably linked nucleic acid in a plant, and the use of the isolated nucleic acid according to the invention, or the recombinant gene comprising the nucleic acid having fungal rust-inducible promoter activity to alter biotic or abiotic stress tolerance, root architecture, nutrient use efficiency, or yield in a plant. In a further embodiment, said plant is a cotton, a soybean or a wheat plant. Also provided is the use 
of the isolated nucleic acid according to the invention to identify other nucleic acids comprising root-preferential, stress-inducible or stress-induced root-preferential promoter activity.

Yet another embodiment provides a method of producing food, feed, or an industrial product comprising (a) obtaining the plant or a part thereof, according to the invention; and (b) preparing the food, feed or industrial product from the plant or part thereof. In another embodiment, said food or feed is oil, meal, ground or crushed seeds, soybean flakes, grain, starch, flour or protein, or said industrial product is biofuel, fiber, industrial chemicals, a pharmaceutical or a nutraceutical. Such food, feed or industrial products contain the root-preferential, stress-inducible and stress-induced root-preferential promoter described herein.

The present invention provides a method to increase lint yield and a method to increase seed yield. In a further embodiment the increase yield compared to a control plant is at least 5%.

"Control plant" as used herein refers to a plant genetically resembling the tested plant but not carrying the recombinant gene, such as wild type plants or null segregant plants.

The transformed plant cells and plants obtained by the methods described herein may be further used in breeding procedures well known in the art, such as crossing, selfing, and backcrossing. Breeding programs may involve crossing to generate an FI (first filial) generation, followed by several generations of selfing (generating F2, F3, etc.). The breeding program may also involve backcrossing (BC) steps, whereby the offspring is backcrossed to one of the parental lines, termed the recurrent parent.

Accordingly, also disclosed herein is a method for producing plants comprising the recombinant gene disclosed herein comprising the step of crossing the plant disclosed herein with another plant or with itself and selecting for offspring comprising said recombinant gene.

The transformed plant cells and plants obtained by the methods disclosed herein may also be further used in subsequent transformation procedures, e. g. to introduce a further recombinant gene.

"Isolated nucleic acid", used interchangeably with "isolated DNA" as used herein refers to a nucleic acid not occurring in its natural genomic context, irrespective of its length and sequence. Isolated DNA can, for example, refer to DNA which is physically separated from the genomic context, such as a fragment of genomic DNA. Isolated DNA can also be an artificially produced DNA, such as a chemically synthesized DNA, or such as DNA produced via amplification reactions, such as polymerase chain reaction (PCR) well known in the art. Isolated DNA can further refer to DNA present in a context of DNA in which it does not occur naturally. For example, isolated DNA can refer to a piece of DNA present in a plasmid. Further, the isolated DNA can refer to a piece of DNA present in another chromosomal context than the context in which it occurs naturally, such as for example at another position in the genome than the natural position, in the genome of another species than the species in which it occurs naturally, or in an artificial chromosome.

The phrases "DNA", "DNA sequence," "nucleic acid sequence," "nucleic acid molecule" "nucleotide sequence" and "nucleic acid" refer to a physical structure comprising an orderly arrangement of nucleotides. The DNA sequence or nucleotide sequence may be contained within a larger nucleotide molecule, vector, or the like. In addition, the orderly arrangement of nucleic acids in these sequences may be depicted in the form of a sequence listing, figure, table, electronic medium, or the like.

As used herein "comprising" is to be interpreted as specifying the presence of the stated features, integers, steps or components as referred to, but does not preclude the presence or addition of one or more features, integers, steps or components, or groups thereof. Thus, e.g., a nucleic acid or protein comprising a sequence of nucleotides or amino acids, may comprise more nucleotides or amino acids than the actually cited ones, i.e., be embedded in a larger nucleic acid or protein. A recombinant gene comprising a nucleic acid which is functionally or structurally defined, may comprise additional DNA regions etc. However, in context with the present disclosure, the term "comprising" also includes "consisting of.

The sequence listing contained in the file named "BCS174006_ST25.txt", which is 5.53 kilobytes (size as measured in Microsoft Windows®), contains 7 sequences SEQ ID NO: 1 through SEQ ID NO: 7 is filed herewith by electronic submission and is incorporated by reference herein.

SEQUENCE LISTING

SEQ ID NO: 1: Nucleotide sequence of the promoter of *Glycine max* inducible by *Phakopsora pachyrhizi*

SEQ ID NO: 2: Forward primer sequence for PCR amplification of transcripts of the gene under control of the promoter of SEQ ID NO:1 in *Glycine max*

SEQ ID NO: 3: Reverse primer sequence for PCR amplification of transcripts of the gene under control of the promoter of SEQ ID NO:1 in *Glycine max*

SEQ ID NO: 4: Forward primer sequence for PCR amplification of transcripts of the gene coding for the actin protein in *Glycine max*

SEQ ID NO: 5: Reverse primer sequence for PCR amplification of transcripts of the gene coding for the actin protein in *Glycine max*

SEQ ID NO: 6: Forward primer sequence for PCR amplification of transcripts of the gene coding for the metalloprotease enzyme in *Glycine max*

SEQ ID NO: 7: Reverse primer sequence for PCR amplification of transcripts of the gene coding for the metalloprotease enzyme in *Glycine max*

Figure 1:
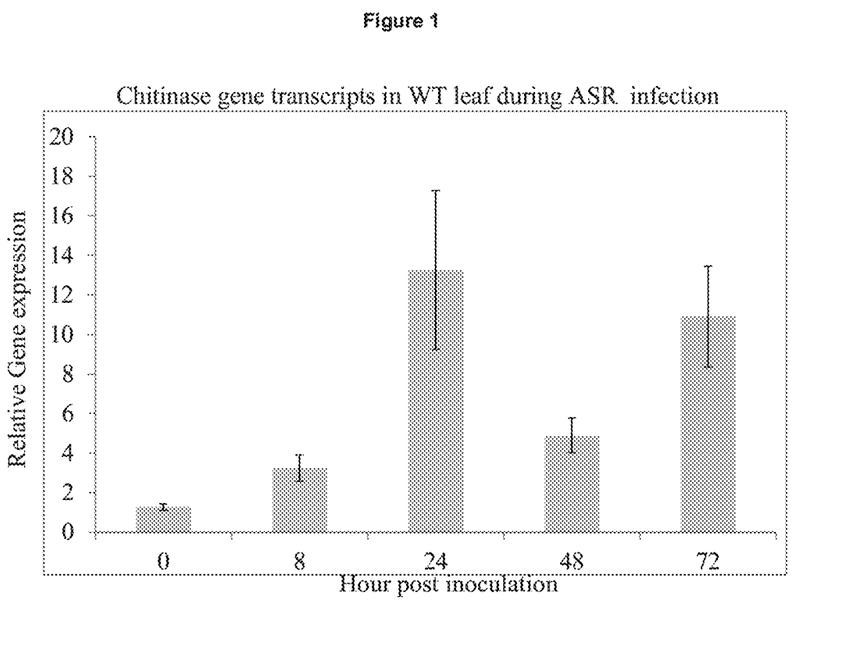
FIG. 1: Accumulation of chitinase gene transcript in soybean leaf during *P. pachyrhizi* infection. Transcript abundance (via qRT-PCR) from individual leaves of soybean after *P. pachyrhizi* inoculation at 0, 8, 24, 48 and 72 hour post infection (hpi). The chitinase gene level is compared to reference mRNA levels and then normalized by mock treatment at each measurement time. Mock and *P. pachyrhizi* inoculations are realized on the same leaf. Bars indicate standard error of 4 biological replicates, Stars represent a significant difference compared to 0 hpi, using Students t-test (*for $p<0.05$; **for $p<0.01$).

FIG. 2: Induction of chitinase gene promoter during *P. pachyrhizi* infection. Relative fluorescence intensity quantification of WT and Promoter-GFP (event 133 and 129) leaves on pathogen (+) or mock (−) inoculation areas. Observation at 24 hours post treatment. Mean values of 9 inoculations (3 inoculations on 3 plants by events). Bars indicate standard error of the 9 replicates.

FIG. 3: Induction of chitinase gene promoter during *P. pachyrhizi* infection. Relative fluorescence intensity quantification of WT and Promoter-GFP (events 133 and 129) leaves on on pathogen (+) or mock (−) inoculated areas. Observations at 24, 48 and 72 hours post treatment. Mean values of 2 inoculations.
Figure 2:
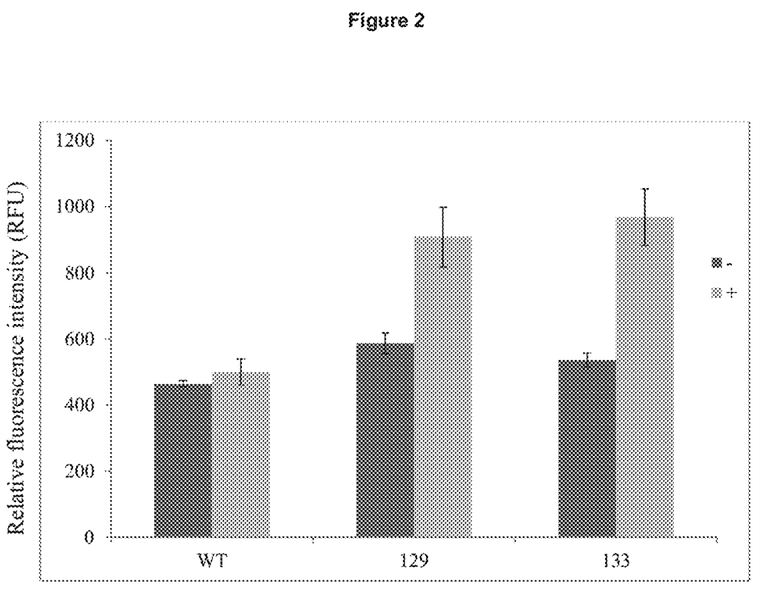
Figure 3:
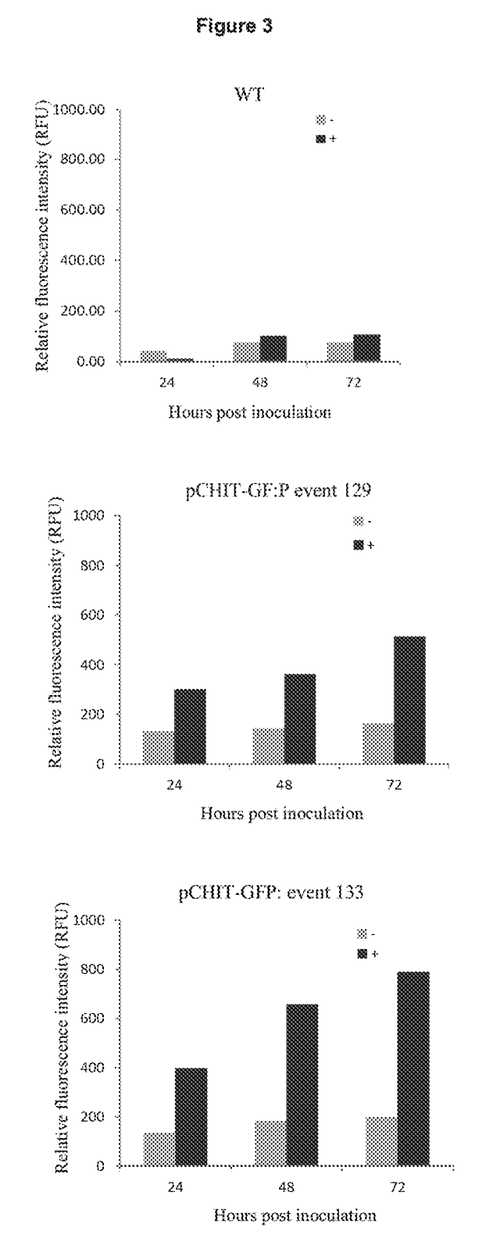

The various aspects of the invention will be understood more fully by means of the experimental examples below.

All the methods or operations described below are given by way of example and correspond to a choice, made among the various methods available for achieving the same result. This choice has no effect on the quality of the result, and, consequently, any appropriate method can be used by those skilled in the art to achieve the same result. In particular, and unless otherwise specified in the examples, all the recombinant DNA techniques employed are carried out according to the standard protocols described in Sambrook and Russel (2001, Molecular cloning: A laboratory manual, Third edition, Cold Spring Harbor Laboratory Press, NY) in Ausubel et al. (1994, Current Protocols in Molecular Biology, Current protocols, USA, Volumes 1 and 2), and in Brown (1998, Molecular Biology LabFax, Second edition, Academic Press, UK). Standard materials and methods for plant molecular biology are described in Croy R.D.D. (1993, Plant Molecular Biology LabFax, BIOS Scientific Publications Ltd (UK) and Blackwell Scientific Publications (UK)). Standard materials and methods for PCR (Polymerase Chain Reaction) are also described in Dieffenbach and Dveksler (1995, PCR Primer: A laboratory manual, Cold Spring Harbor Laboratory Press, NY) and in McPherson et al. (2000, PCR-Basics: From background to bench, First edition, Springer Verlag, Germany).

EXAMPLES

Example 1: Transcript Levels of the Chitinase Gene in Soybean after *Phakopsora pachyrhizi* Infection In order to measure transcript levels of the chitinase gene in soybean leaves, qPCR was used. Total RNA was extracted from soybean leaves by using the RNeasy® Plant Mini Kit (QIAGEN) and was treated with TURBO DNA-Free™ Kit (Invitrogen). 1 μg of RNA was used to synthetize cDNA with ThermoScript™ RT-PCR System kit (Invitrogen). The cDNA was diluted with 98 μL of RNAse free water to a final volume of 100 μL. 5 μL of diluted cDNA were used in a 20 μL reaction containing 10 μL of SsoAdvanced™ Universal SYBR® Grenn Supermix (BOI-RAD), 1 μL of primer forward, 1 μL of primer reverse and 3 μL of RNAse free water. qRT-PCR was performed using the LightCycler 480. Primers used to follow the expression of the chitinase gene are listed in Table 1. The thermocycling conditions were as follows: denaturation at 95° C. for 10 minutes and for amplification 45 cycles of 10 seconds at 95° C., 10 seconds at 60° C. and 10 seconds at 70° C. After the final cycle, the dissociation curve analysis was carried out to verify that the amplification occurred specifically and that no primer dimer product has been generated during the amplification process. The actin and metalloprotease genes (primer sequences in table 1) were used as endogenous reference genes to normalize the calculation using the Comparative Ct value method. The level of transcript abundance relative to the reference gene (termed ΔCt) was determined according to the function ΔCt=Ct (test gene)−Ct (reference gene). Then the function ΔΔCt was first determined using the equation ΔΔCt=ΔCt (treatment)−ΔCt (control) (where control represented mock-treated plants). The ratio of treatment/control was calculated by the equation 2^(−ΔΔCt). All calculations have been realized with LightCycler® 480SW15 software.

TABLE 1

Primer sequences for qRT-PCR

| Gene | Primer name | Primer sequence | Amplicon length |
|---|---|---|---|
| Actin | GmACTIN_F | CGGTGGTTCTATCTT GGCATC (SEQ ID NO: 4) | 142 pb |
| | GmACTIN_R | GTCTTTCGCTTCAAT AACCCTA (SEQ ID NO: 5) | |
| Metallo-protease | Gmcons7_F* | ATGAATGACGGTTCC CATGTA (SEQ ID NO: 6) | 114 pb |
| | Gmcon7_R* | GGCATTAAGGCAGCT CACTCT (SEQ ID NO: 7) | |
| Predicted chitinase | GmCHIT_F | GAGATTAACGGTGCA TCAGG (SEQ ID NO: 2) | 330 pb |
| | GmCHIT_R | ATTAACACGAGCCTG AACAGTACT (SEQ ID NO: 3) | |

*from Hirschburger et al., 2015

Transcript levels were analyzed at 0 h, 8 h, 24 h, 48 h and 72 h post-infection by *P. pachyrhizi*. The results are reported in FIG. 1, showing significant increases in the levels of transcription of the gene from 8 h up to 72 h post-infection, thereby demonstrating the induction of the promoter of this gene following infection by *P. pachyrhizi*.

Example 2: Promoter Activity After Treatment with Various Elements

2.1. Construction of a Reporter Gene for Monitoring the Promoter Activity

A DNA fragment of 3 454 bp upstream of the chitinase gene coding sequence, considered to comprise the putative promoter, was synthetized with addition of AatII and PlmII restriction enzyme sites respectively at the 5' and 3' end of the sequence. The putative promoter was cloned, using the restriction enzyme sites, to drive the expression of a GFP (Green-Fluorescent Protein) coding sequence in a vector also containing the gene coding for the HPPD enzyme (4-Hydroxyphenylpyruvate dioxygenase) under the control of a p35S promoter (used as selectable marker for plant transformation). The new vector obtained was named pBay00457. One positive clone was then sequenced from left border (LB) to right border (RB), and the T-DNA transferred to the plant via *Agrobacterium tumefaciens* transformation.

2.2. Soybean Treatment and Pathogens Inoculation

For the phytohormone assays, two leaves of wild-type (WIT positive control or T1 plants transformed with the vector pBay00457 (containing 2 copies of the transgene) were harvested and placed on Watman filter with cotton around the petiole. One leaf was spread with chemicals inducer of phytophormone pathway (+) and one leaf was mock treated (−).

For Jasmonate (JA) pathway activation, the leaves were sprayed with EC4% and methyl JA analogue (coronatine) at 3 ppm (+), or EC4% only (−).

For Salicylate (SA) pathway activation, the leaves were treated with 2.5 mM of SA in Ethanol 10% (+), or Ethanol 10% only (−).

For Ethylene (ET) pathway activation, the leaves were treated with the ethylene precursor (1-aminocyclopropane-1-carboxylic acid: ACC) at 20 mM (+) or $H_2O$ (−).

Wounding was realized by cutting 3 leaf discs (0.3 cm of diameter) on a leave of WT plant, and on a leave of transformed "promoter-GFP" plant.

Inoculations of *P. pachyrhizi* were realised via agar plugs (0.5 cm diameter). Cryo-conserved spores were first rehydrated 24 h before infection. 2 ml of a solution at 1 mg of spores/ml was equally spread on a plate of agar 3%, allowing a concentration of 600 spores/plug. Plugs were put on cut leaves which were incubated at 24° C., humidity 80% and 24 h in the dark, followed by a photoperiod 12/12. Plugs were removed 24 h post inoculation Inoculations of *Sclerotinia sclerotiorum* were realized with an agar plug of 5 days old fungus mycelium. Leaves were placed at 24° C., saturated humidity and photoperiod 12/12. Plugs were removed 48 hours post inoculation.

Mock and pathogen inoculations were realized on the same leaf, with 3 mock inoculations on the left side and 3 inoculations with the fungus on the right side of the leaf.

2.3. GFP Observations

The expression of green fluorescence rapporteur gene, GFP, under the control of the promoter according to the invention was measured in two soybean transformation events (events 133 and 129). Expression of the GFP was visualized with a macroscope camera LEICA Z16APO equipped with a GFP filter, lens 1×, magnification 6.95×, exposure time 1 s, gain 3. Fluorescence quantification was performed with MetaMorph software.

For leaves infected by *P. pachyrhizi*, fluorescence observations were done at 0, 24, 48, and 72 hours post infection.

For leaves infected by *S. sclerotiorumn*, fluorescence observations were done at 0, 48, and 72 hours post infection.

For leaves either wounded or treated with the phytohormones, fluorescence observations were done at 0, 48, and 72 hours respectively post-wounding and post-treatment.

A T2 homozygous soybean plant containing the GFP under the control of a promoter known to be responsive to biotic and abiotic stress (construct pBay00174, containing the promoter PDF1.2 from *Arabidopsis*, described in Manners et al. 1998, Plant Mol. Biol. 38: 1071-1080), was used as positive control. Results are shown in Table 2.

TABLE 2

Expression profile of Promoter-GFP construct

| | | Biotic stress | | Abiotic | Phytohormones | | |
|---|---|---|---|---|---|---|---|
| | | *Phakopsora* | *Sclerotinia* | stress | pathway induction | | |
| Construct | Event | *pachyrhizi* | *sclerotiorum* | Wounding | JA | ET | SA |
| pBay00457 | 129 | + | − | +(1) | − | − | − |
| | 133 | + | nd | +(1) | − | − | − |
| Ø | WT | − | − | − | − | − | − |
| pBay00174 | Positive control | + | + | +(2) | + | + | −(3) |

Ø: absence of construct;
−: no difference in GFP fluorescence observed after treatment;
+: GFP fluorescence increase after treatment;
nd: not determined
(1)local response at the site of wounding only, no propagation
(2)local and propagated response
(3)the promoter used for the positive control (PDF1.2) is known not to be responsive to SA The results shown in Table 2 demonstrate that the promoter according to the invention is specifically induced by infection of the soybean plant with *Phakopsora pachyrhizi*, whereas it is not induced by the fungus *Sclerotinia sclerotiorum*. These results also demonstrate that this promoter is not induced by most of the elements known to induce a defense response in plants, in particular a treatment with the phytohormones jasmonic acid, salicylic acid and ethylene. Finally, when it comes to the response to wounding, the results show that the promoter is activated locally at the point of wounding only.

These experiments demonstrate the apparent specificity of this promoter to infection by *P. pachyrhizi.*

2.4. Promoter Expression Over Time after Infection by *P. pachyrhizi*

The expression of GFP under the control of the promoter according to the invention was measured in two soybean transformation events (events 133 and 129) at 24 h, 48 h and 72 h post-infection by *P. pachyrhizi*. The results are reported in FIGS. 2 and 3.

The results demonstrate the rapid induction of the promoter activity 24 h after infection by *P. pachyrhizi* (FIGS. 2 and 3), and its continuous activity over time at 48 h and 72 h post-infection (FIG. 3).

Example 3: Identification of Orthologous Promoters

The fungal rust-inducible promoter according to the invention can be used to identify orthologous promoters, i.e. promoters having a substantially identical nucleic acid sequence and the same fungal rust-inducible functionality.

This can, for example, be done, in silico, by looking into genomic databases for nucleic acid sequences having a substantially identical nucleic acid sequence in other plant species. For example, fungal rusts are known to infect many plant species, and therefore similar promoters with similar functionalities can be identified in such other species.

Also, the Asian Soybean Rust, *Phakopsora pachyrhizi*, is known to infect other host plants than the soybean *Glycine max*, like e.g. *Cajanus cajan, Lupinus* sp., *Phaseolus vulgaris* or *Vigna unquiculata*, in which similar promoters with similar functionalities can also be identified.

The invention claimed is:

1. A recombinant expression cassette comprising the nucleotide sequence of SEQ ID NO: 1 or a functional fragment thereof, operably linked to a heterologous nucleic acid encoding an expression product of interest, and optionally a transcription termination and polyadenylation sequence functional in plants.

2. The recombinant expression cassette according to claim 1, wherein the expression product of interest is a protein, or an RNA molecule capable of modulating the expression of a gene.

3. A soybean host cell, comprising the recombinant expression cassette according to claim 1.

4. A soybean plant, comprising the recombinant expression cassette of claim 1.

5. Plant parts and seeds obtainable from the plant according to claim 4.

6. A method of producing a transgenic soybean plant, comprising the steps of:
   a) introducing or providing the recombinant expression cassette according to claim 1 to a plant cell to create transgenic plant cells; and
   b) regenerating transgenic plants from said transgenic cells.

7. A method of effecting fungal rust-inducible expression of a nucleic acid, comprising introducing the recombinant expression cassette according to claim 1 into the genome of a plant.

8. The recombinant expression cassette according to claim 1, wherein the recombinant expression cassette comprises the nucleotide sequence of SEQ ID NO: 1.

9. The recombinant expression cassette according to claim 1, wherein the recombinant expression cassette comprises a functional fragment of SEQ ID NO: 1.

10. A method of conferring, in a soybean cell, expression of an expression product of interest in response to exposure of the soybean cell to a fungal rust, comprising providing, in the soybean cell, a nucleic acid, wherein the nucleic acid comprises
   a promoter comprising the nucleotide sequence of SEQ ID NO: 1 or a functional fragment thereof, operably linked to a nucleic acid sequence encoding the expression product of interest,
   wherein the nucleic acid sequence encoding the expression product of interest is heterologous to the promoter.

11. A soybean plant exhibiting fungal rust inducible expression of an expression product of interest, wherein the soybean plant comprises, in the genome of at least a cell, the recombinant expression cassette according to claim 1.

12. The soybean plant of claim 11, wherein the expression product of interest is
   a protein, or
   an RNA molecule capable of modulating the expression of a gene.

* * * * *